United States Patent [19]

Staffin et al.

[11] Patent Number: 4,519,718
[45] Date of Patent: May 28, 1985

[54] METHOD AND APPARATUS FOR THERMAL TESTING

[75] Inventors: H. Kenneth Staffin, Colonia; Robert B. Roaper, Martinsville; Karin S. Bickford, Plainsboro, all of N.J.

[73] Assignee: Procedyne Corp., New Brunswick, N.J.

[21] Appl. No.: 401,090

[22] Filed: Jul. 23, 1982

[51] Int. Cl.$^3$ ............................................. F26B 17/10
[52] U.S. Cl. ...................................... 374/45; 34/57 A; 432/58
[58] Field of Search .................... 34/57 A, 62; 374/45, 374/57 A, 4, 5; 432/15, 58, 261

[56] References Cited

U.S. PATENT DOCUMENTS 3,851,406 12/1974 Dumitru et al. ...................... 432/58
4,054,376 10/1977 Wareham ............................... 432/15
4,151,399 4/1979 Beale ..................................... 432/58
4,320,795 3/1982 Gwyn et al. ......................... 34/57 A

FOREIGN PATENT DOCUMENTS 1473700 11/1969 Fed. Rep. of Germany ........ 374/45
8102585 9/1981 Sweden ............................... 34/57 A Primary Examiner—Richard R. Stearns
Assistant Examiner—W. Morris Worth
Attorney, Agent, or Firm—Kane, Dalsimer, Kane, Sullivan and Kurucz

[57] ABSTRACT

A device for thermal shock testing and thermal cycling of workpieces is provided which comprises at least one fluidized bed chamber for thermally treating a workpiece. Agitation of the area about the workpiece is accomplished by movement of the workpiece, by baffles, or by providing a supplementary gas distributor. The agitation provided increases the flow rate of particles of the fluidized bed particulate media in a localized area about the workpiece, thus increasing the rate of heat transfer between the bed media and the workpiece, and increasing thermal shock capacity of the thermal shock tester.

5 Claims, 5 Drawing Figures

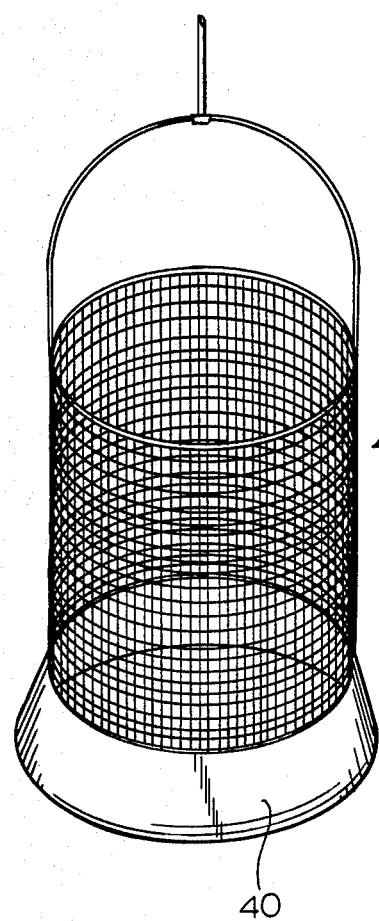
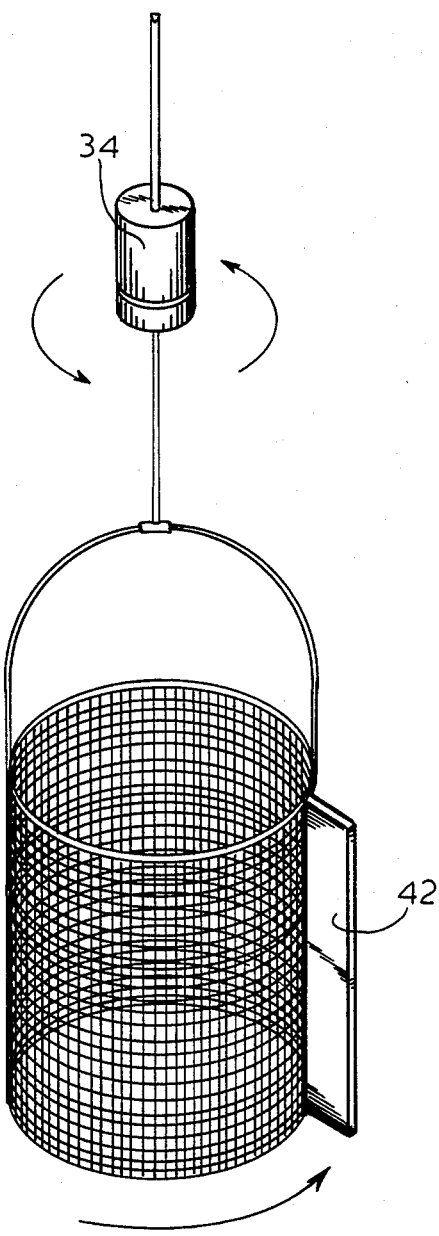

METHOD AND APPARATUS FOR THERMAL TESTING

The present invention relates to the field of thermal testing and, more specifically, to devices for causing rapid changes in the temperature of a workpiece.

BACKGROUND OF THE INVENTION

Generally, thermal shock testing involves subjecting an article to be tested, i.e., the workpiece, to sudden heating and cooling by moving it to and from separate hot and cold environments. Thermal cycling tests involve changing the temperature of the environment without moving the workpiece. These and related methods are hereinafter referred to collectively as thermal testing unless the context indicates otherwise.

Thermal testing is extremely useful for evaluating the reliability of materials and devices because the thermal stresses created in such workpieces by sudden temperature changes tend to accelerate failures due to defects that would otherwise be undetectable until long after manufacture. For example, thermal testing is widely used in the electronics industry to detect defective semiconductor-devices before they are installed in complex electronic systems where failure could result in expensive repairs and considerable down time.

A typical prior art device for conducting thermal testing would have an enclosed heat transfer medium provided with a heating means, e.g., electric resistance heaters, and/or a cooling means, e.g., gas expansion refrigeration. Specifically, a thermal cycling device would have a single heat transfer media enclosure with both heating and cooling means, and a thermal shock device would have two such enclosures, one for cooling and the other for heating. In operation, the workpiece is simply submerged in the heat transfer media for a fixed period of time, and its temperature changes until it approaches thermal equilibrium with the heat transfer media.

The nature of the heat transfer media is a dominant factor in how fast the workpiece is heated or cooled, i.e., the rate at which the system approaches thermal equilibrium. Gaseous heat transfer media, usually air, have the advantages of being inexpensive and do not contaminate the workpiece avoiding subsequent cleaning operations before use. However, the heat transfer characteristics of gases are slow and hence they cannot change a workpiece's temperature fast enough to create sufficient thermal stresses to satisfactorily accelerate failures due to latent defects in the workpiece.

Liquids unlike gases, have very fast heat transfer characteristics and high heat capacities. Therefore, they make excellent heat transfer media for thermal testing. A workpiece submerged in liquid heat transfer media rapidly reaches thermal equilibrium with the system and sufficient thermal stresses to induce failure of the workpiece due to latent defects are attained. However, liquids also have drawbacks that make them undesirable for many thermal testing applications. Specifically, since suitable liquids that are stable at the temperatures contemplated for thermal testing, usually −65° C. to 200° C., are usually very expensive and evaporation, dripping, and carryout losses are usually large, rendering the costs of such testing very high.

Volatility and toxicity of such liquids may also pose serious health hazards, fire hazards, and problems with governmental regulatory agencies as well. An additional problem with liquid heat transfer media in thermal testing devices is that the liquid may have to be cleaned from the workpiece to avoid problems in subsequent use, e.g., soldering.

Moreover, since few, if any, liquids would be suitable for both extremely high and extremely low temperature applications some thermal shock systems using different high and low temperature liquid heat transfer media, i.e., liquid/liquid systems, and are subject to cross-contamination caused by carryover when the workpiece is moved from one liquid to the other.

SUMMARY OF THE INVENTION

The above disadvantages of liquid and gas thermal testing systems are obviated by the present invention by use of a fluidized bed, i.e., a particulate solid suspended in a gas, as the heat transfer medium.

Since the mid-1940's, fluidized beds have found use in coal gasification, catalytic cracking in the petroleum industry and a variety of other process applications.

The fluidizing process causes a particulate solid bed to become an expanded suspended mass that behaves like a boiling liquid having a zero angle of repose, seeking its own level and assuming the shape of the vessel it is contained in. This expanded mass state is accomplished by passing a gas upwardly through a particulate solid in an enclosure at sufficient velocity to suspend the expanded mass so that it exhibits characteristics usually associated with low viscosity fluids. Fluidized solids exhibit no significant changes in physical properties over a wide range of temperatures and are not subject to melting point or boiling point limitations associated with liquids used at conventional thermal testing temperatures. Consequently, the same solid bed media may be useful for both heating and cooling operations and the cross contamination, discussed above, is totally eliminated. Any bed media adhering to a workpiece after testing is easily removed before subsequent use, by a light dusting. Moreover, suitable non-toxic, easily recovered bed media like aluminum oxides, zirconium oxides and the like are readily available and inexpensive.

As noted above, the heat transfer rate between the workpiece and the transfer media is the dominant factor with respect to how fast the workpiece is heated or cooled and hence the amount of thermal stress experienced by the workpiece. Therefore, increasing the heat transfer rate improves the effectiveness of thermal testing.

It has been found that moving the workpiece and/or its support means with respect to the fluidized bed media during heating and cooling operations accelerates heat transfer from the bed media to the workpiece. Providing agitator means, e.g., baffles, blades, or the like, that operate independently and/or cooperate with the means for moving the workpiece within the heat transfer media's enclosure during heating and cooling operations, increases turbulence in the bed media about the workpiece, thereby accelerating the heat transfer rate. The effects of moving the workpiece with respect to the bed media and agitator enhanced turbulence, make it possible to create thermal stresses with fluidized beds heretofore only thought possible with liquid/liquid systems.

It is an object of the present invention to provide a fluidized bed thermal testing device that produces thermal stresses approaching or greater than those produced by liquid/liquid systems.

It is another object of this invention to provide a thermal testing device that is easy to use and inexpensive to operate.

It is another object of the present invention to provide a thermal testing device that is not subject to cross-contamination problems.

It is another object of the present invention to provide a thermal testing device that utilizes a non-toxic, non-volatile heat transfer media.

With the above and other incidental objects and advantages in view as will more fully appear in the specification, the invention intended to be protected by Letters Patent consists of the features of construction, the parts and combinations thereof, and the mode of operation as hereafter described or illustrated in the accompanying drawings, or their equivalents.

BRIEF DESCRIPTION OF THE DRAWINGS

Referring to the accompanying drawings wherein are shown some but, obviously, not all embodiments of the present invention.

FIG. 2, is a perspective view of a workpiece support means having a conical baffle.

FIG. 3, is a perspective view of workpiece support means having a paddle type agitator.

The same reference numerals refer to like parts throughout the drawings.

Figure 1:
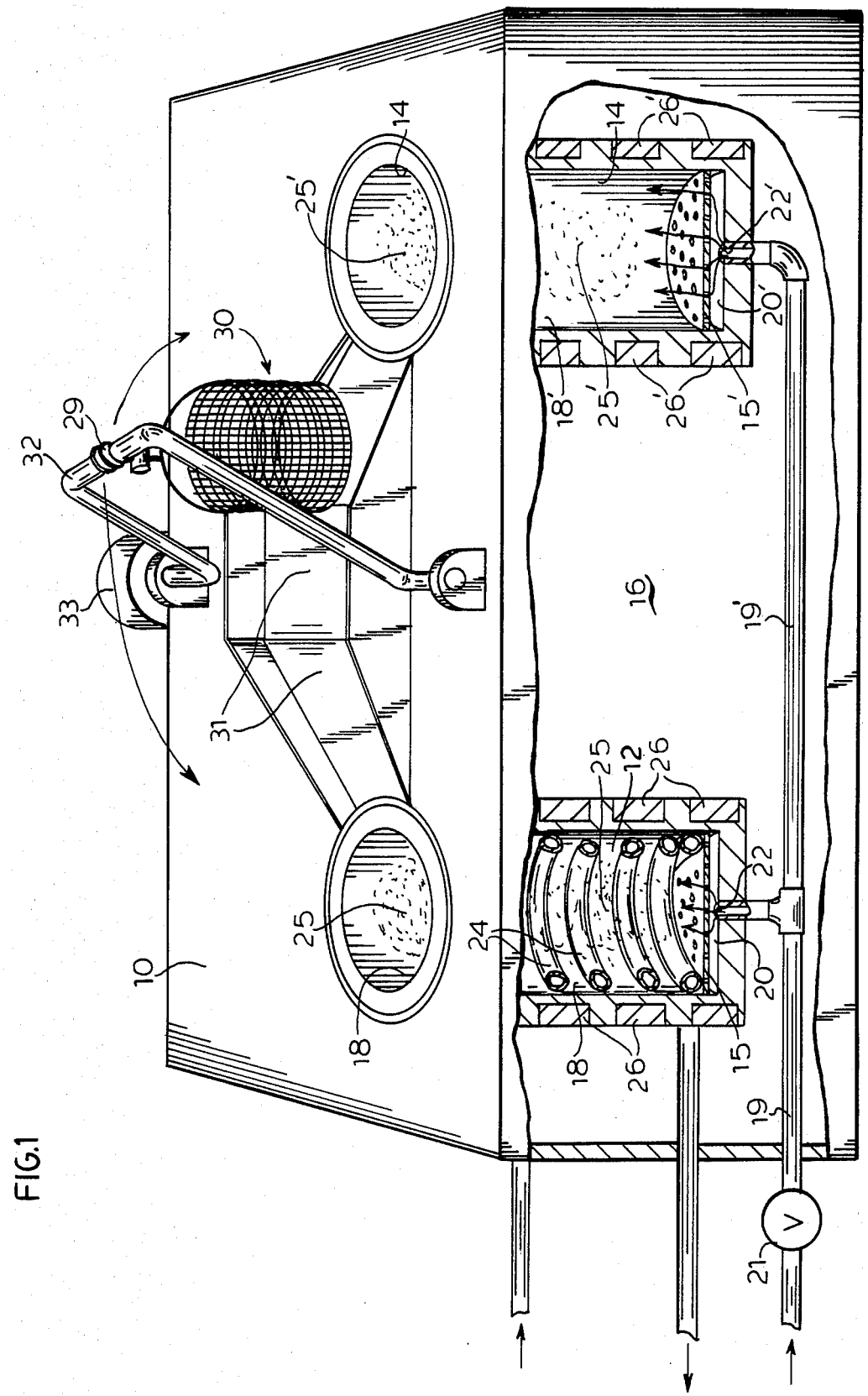
FIG. 1, is a partially cut away perspective view of a thermal testing device, constructed in accordance with the present invention, utilizing a fluidized bed, and a rotating workpiece support means.

Thermal shock tester 10 illustrated in FIG. 1 is provided with two independent fluidized bed enclosures 12 and 14 for performing cooling and heating operations, respectively. The enclosures 12 and 14 are separated by thermally insulating material 16.

The cooling enclosure 12 comprises a heat transfer portion 18 and a plenum 20 separated by distributor plate 15. Conduit 19, inlet 22, and valve 21 provide means for supplying a regulated flow of fluidizing gas to plenum 20. Heaters 26 disposed on the exterior walls of enclosure 12 and cooling coils 24 disposed within the enclosure 12 provide means for controlling the temperature within enclosure 12.

The heating enclosure 14 resembles cooling enclosure 12 in all respects except that no cooling coils 24 are provided therein. Parts of heating enclosure 14 corresponding to like parts of cooling enclosure 12 are indicated by the same reference numerals primed.

Workpiece support means, e.g., basket 30, supports one or more workpieces 31 to be heated and cooled in the enclosures 14 and 12. The basket 30 is suspended on a swivel connection 29 from the electromechanical transfer arm 32 so that it may be positioned in either enclosure by simple movement of the transfer arm. A means for rotating the basket 30 within the enclosures 12 and 14, e.g., electric motor 34, is disposed between the swivel 29 and basket 30.

In operation, a fluidizing gas, e.g., nitrogen, air, or the like flows into the respective plenums 20, 20' at a selected rate via valve 21 conduits 19, 19', and inlets 22, 22'. The gas flows upwardly through distributor plates 15, 15' entering heat transfer portions 18, 18' of enclosures 12 and 14. The upwardly moving gas causes bed media particles, e.g., aluminum oxides, zirconium oxide or the like, disposed therein to levitate producing expanded masses 25, 25' that behave like a liquid. Accurate temperature adjustment of the expanded mass 25 in the cooling enclosure 12 is accomplished by circulating coolant through cooling coils 24 at maximum capacity and adjusting up to the desired temperature, e.g., $-65°$ C. with heaters 26. The temperature of the heating enclosure 14', e.g., 150° C., is controlled by heaters 26' alone.

A workpiece 31 to be tested is placed in basket 30 and the electromechanical means 33 for controlling arm 32 is then activated. The electromechanical means 33 automatically swings arm 32 from a rest position wherein the basket 30 suspended therefrom, as described above, is submerged in the cooled expanded mass 25 in enclosure 12 to a second rest position wherein the basket 30 is submerged in the heated expanded mass 25' in enclosure 14. The electromechanical means 33 is provided with a variable timer so that the intervals between transfers from enclosure 12 to enclosure 14 and vice versa may be set, as desired by an operator, for the specific test to be performed. It is to be understood that the number of transfers between enclosures 12 and 14 and the time intervals between them are a matter of choice for the operator and selected in accordance with the specific test employed or protocol prescribed or established. A typical test would involve alternate submersions of the workpiece in the cooling expanded mass 25 for 5 minutes and then in the heating expanded mass 25' for 5 minutes. The transfer time, i.e., when the basket 30 is not fully submerged in either basket during a test, may be about 10 seconds.

The rate of heat transfer between the workpiece and the expanded mass 25, 25' is normally about 30 to 50 BTU/hr ft$^2$; but, when turbulence in the expanded mass in the vicinity of the workpieces is increased in accordance with the present invention, heat transfer rates exceeding or approaching those of many liquids, e.g., 80 to 120 BTU/hr. ft.$^2$, can be attained.

The turbulence in expanded masses 25, 25' may be increased by causing the basket 30 to move during submersion in the expanded masses 25, 25'. In the embodiment shown in FIG. 1 basket 30 is rotated along its cylindrical axis by motor 34 during submersion in both enclosures 12 or 14. The rotation may be automatically stopped during transfer from one enclosure to the other by any suitable switching means.

Figure 4:
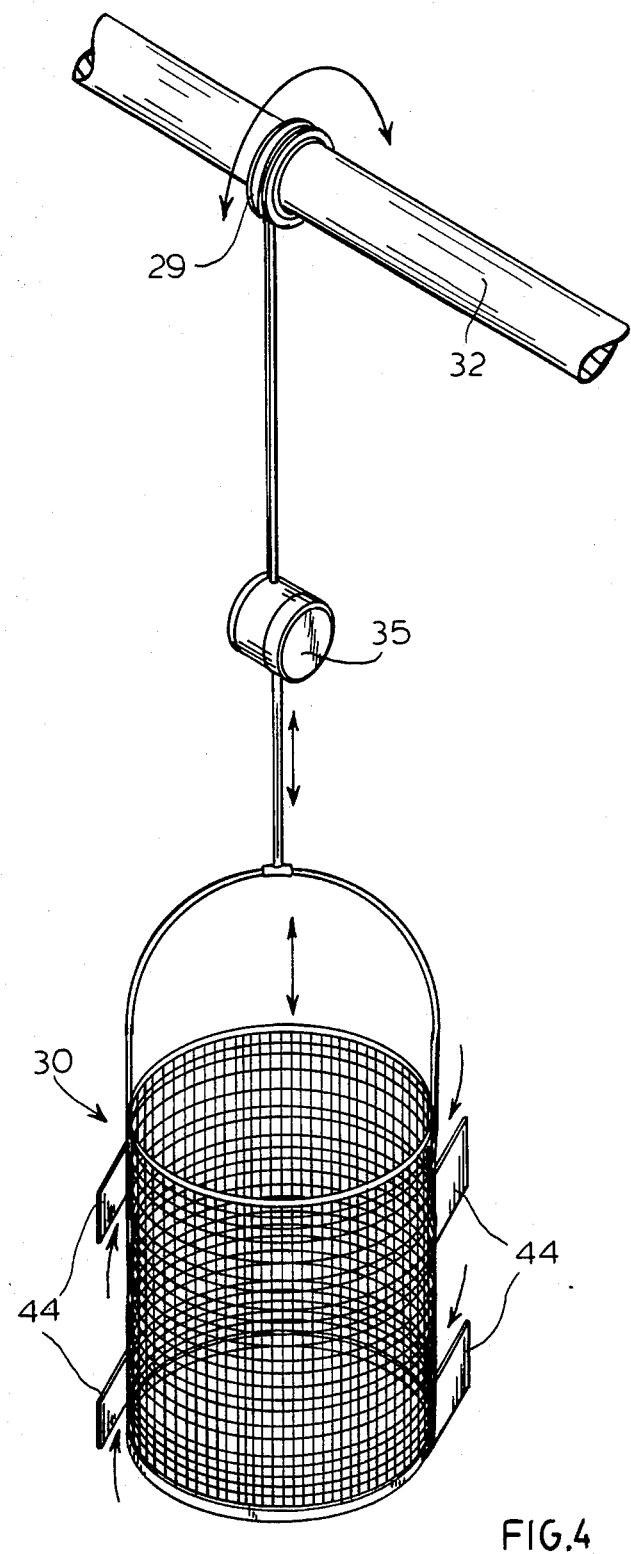
FIG. 4, is a perspective view of a workpiece support means having angular tab-like agitators.

The embodiment shown in FIG. 4 contemplates an oscillating means 35 for moving the basket 30 within the enclosures 12 and 14 vertical plane, i.e., up and down, instead of rotating with motor 34, during submersion in enclosure 12 and 14 to increase turbulence. It will be appreciated that a combination of motor 34 and oscillator 35, or the like, could be used together so that the basket 30 would be capable of both rotation and oscillation.

Turbulence in the vicinity of the workpiece 31 may also be increased with baffles that concentrate fluid flow within the expanded masses 25, 25' in that area. FIG. 2 shows a basket 30 having an upwardly tapering conical baffle 40 attached to its lower end. During submersion the conical baffle 40 directs the upwardly moving fluid flow originating at the distributor plates 15, 15' toward its central region, i.e., the vicinity of the workpiece 31.

The basket 30 shown in FIGS. 3 and 4 are provided with agitators 42 and 44. These agitators are designed to cooperate with the movement of the basket 30 causing increased turbulence in the vicinity of a workpiece disposed therein. As basket 30 is rotated about its cylindrical axis in expanded masses 25 or 25' as indicated by the arrows in FIG. 3, the agitator 42 changes the direction of and increases overall fluid flow thereby producing additional turbulence in the central area to be occupied by the workpiece. The agitators 44 likewise change the direction of and increase fluid flow in response to vertical movement of the basket 30.

Figure 5:
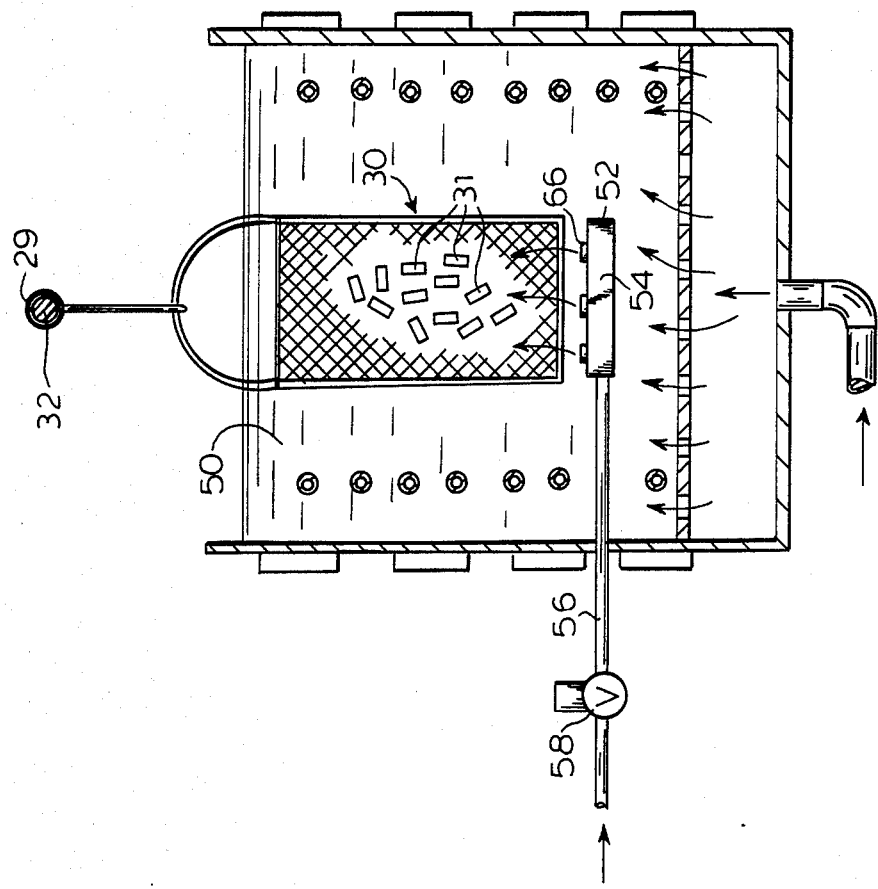
FIG. 5, is a fragmentary cross sectional view of an alternate embodiment of the present invention.

Another means for increasing turbulence in the workpiece area of an enclosure 50 constructed in the same manner as cooling enclosure 12 is providing a supplementary fluidizing gas distributor 52 beneath the support basket 30 as shown in FIG. 5. The fluidizing gas is supplied to the supplementary plenum 54 through conduit 56 and its flow is regulated by valve 58. Supplementary distributor plate 66 directs and distributes the flow of supplementary fluidizing gas to the workpiece area.

This significantly increases turbulence in the vicinity of the workpiece 31 and therefore, heat transfer between the fluidized expanded mass 25 or 25' is appreciably improved.

It is to be understood that a fluidized bed enclosure, e.g., enclosures 12 or 50 provided with both heating and cooling means could itself be cycled between high and low temperatures eliminating the transfer step for some operations.

While in order to comply with the statute, this invention has been described more or less specifically as to structure but it's to be understood that the invention is not limited to the specific features described and that the means and constructions disclosed herein are but a few of many modes of practicing the present invention which is, therefore, claimed in any of its forms or modifications within the legitimate and valid scope of the appended claims.

What is claimed is:

1. A device for thermal testing, which comprises:
    a first enclosure for an expanded mass of solid particles suspended in a fluidizing gas that behaves like a liquid;
    a second enclosure for an expanded mass of solid particles suspended in a fluidizing gas that behaves like a liquid;
    a least one temperature adjustment means provided for controlling the temperature of each enclosure;
    a support means for supporting a workpiece in one of the first or second enclosures and adapted to transfer the workpiece from one enclosure to the other;
    an agitating means affixed to the support means for agitating the support means in order to increase turbulence in the vicinity of the workpiece.

2. A device for thermal testing, which comprises:
    a first enclosure for an expanded mass of solid particles suspended in a fluidizing gas that behaves like a liquid;
    a second enclosure for an expanded mass of solid particles suspended in a fluidizing gas that behaves like a liquid;
    at least one temperature adjustment means provided, for controlling the temperature of each enclosure;
    a support means for supporting a workpiece in one of the first or second enclosures and adapted to transfer the workpiece from one enclosure to the other; and
    at least one baffle affixed to the support means for detecting fluid flow of the expanded mass in order to increse turbulence in the vicinity of the workpiece during thermal operations.

3. A device for thermal testing, which comprises:
    a first enclosure for an expanded mass of solid particles suspended in a fludizing gas that behaves like a liquid, the fluidizing gas being supplied to the enclosure by a first supply means;
    a second enclosure for an expanded mass of solid particles suspended in a fluidizing gas that behaves like a liquid, the fluidizing gas being supplied to the enclosure by a second supply means;
    at least one temperature adjustment means provided for controlling the temperature of each enclosure;
    a support means for supporting a workpiece in one of the first or second enclosures and adapted to transfer the workpiece from one enclosure to the other; and
    a supplementary fluidizing gas distributor provided in at least one enclosure located above the associated supply means and below the support means, adapted to increase the flow rate of air toward the workpiece holder.

4. A device for thermal testing as recited in claim 2 or 3, further comprising:
    a transfer means for automatically transferring the support means and workpieces disposed therein from the first enclosure to the second enclosure.

5. A device for thermal testing as recited in claim 2, wherein:
    the baffle is a conically shaped plate affixed to the support means and tapering toward the vicinity of the workpiece.

* * * * *